United States Patent
Baril et al.

(10) Patent No.: US 11,395,660 B2
(45) Date of Patent: Jul. 26, 2022

(54) STACKABLE LIGATION CLIP

(71) Applicant: Covidien LP, Mansfield, MA (US)

(72) Inventors: Jacob C. Baril, Norwalk, CT (US); Justin Thomas, New Haven, CT (US); Roy J. Pilletere, North Haven, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/865,921

(22) Filed: May 4, 2020

(65) Prior Publication Data

US 2021/0038225 A1 Feb. 11, 2021

Related U.S. Application Data

(60) Provisional application No. 62/882,768, filed on Aug. 5, 2019.

(51) Int. Cl.
*A61B 17/122* (2006.01)

(52) U.S. Cl.
CPC ................... *A61B 17/122* (2013.01)

(58) Field of Classification Search
CPC ... A61B 17/122; A61B 17/1222; A61B 17/08; A61B 17/0487; A61B 17/12
See application file for complete search history.

(56) References Cited

U.S. PATENT DOCUMENTS

| | | |
|---|---|---|
| 3,439,523 A | 4/1969 | Wood |
| 3,713,533 A | 1/1973 | Reimels |
| 4,076,120 A | 2/1978 | Carroll et al. |
| 4,146,130 A | 3/1979 | Samuels et al. |
| 4,187,712 A | 2/1980 | Samuels et al. |
| 4,212,303 A | 7/1980 | Nolan |
| 4,212,390 A | 7/1980 | Raczkowski et al. |
| 4,294,355 A | 10/1981 | Jewusiak et al. |
| 4,344,531 A | 8/1982 | Giersch |
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

Chinese International PCT Application No. PCT/CN2018/078294 filed Mar. 7, 2018, Covidien LP.

(Continued)

*Primary Examiner* — Brooke Nicole Labranche

(57) ABSTRACT

A ligation clip includes a first beam that supports a first alignment member and a second beam that supports a second alignment member. The first and second alignment members receive distal end portions of first and second beam portions of a second ligation clip when the ligation clips are stacked within a multi-fire clip applier to provide stability to the clip stack.

18 Claims, 4 Drawing Sheets

(56) References Cited

U.S. PATENT DOCUMENTS

| | | |
|---|---|---|
| 4,487,205 A | 12/1984 | Di Giovanni et al. |
| 4,492,232 A * | 1/1985 | Green .................. A61B 17/128 |
| | | 606/143 |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,942,886 A | 7/1990 | Timmons |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,846,255 A | 12/1998 | Casey |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,349,727 B1 | 2/2002 | Stewart, Jr. |
| 6,391,035 B1 | 5/2002 | Appleby et al. |
| 6,419,682 B1 | 7/2002 | Appleby et al. |
| 6,421,920 B1 | 7/2002 | Jensen |
| 6,439,727 B1 | 8/2002 | Koide |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Taconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 2002/0046961 A1 | 4/2002 | Levinson et al. |
| 2002/0177863 A1 | 11/2002 | Mandel et al. |
| 2002/0198537 A1 | 12/2002 | Smith et al. |
| 2004/0097970 A1 | 5/2004 | Hughett |
| 2004/0199178 A1 | 10/2004 | Small |
| 2005/0033333 A1* | 2/2005 | Smith ................ A61B 17/1285 |
| | | 606/158 |
| 2005/0165422 A1 | 7/2005 | Wilson |
| 2005/0165423 A1 | 7/2005 | Gallagher et al. |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 | 9/2006 | Wilson et al. |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1 | 7/2009 | Whiting |
| 2011/0224700 A1 | 9/2011 | Schmidt et al. |
| 2011/0295291 A1 | 12/2011 | Trivisani |
| 2012/0083803 A1 | 4/2012 | Patel et al. |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0054192 A1 | 2/2014 | Chancibot |
| 2014/0243862 A1 | 8/2014 | Bagaoisan et al. |
| 2014/0276970 A1 | 9/2014 | Messerly et al. |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0209151 A1 | 7/2017 | Brown |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 | 7/2018 | Lebens, III |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |
| 2018/0368852 A1 | 12/2018 | Foshee et al. |
| 2019/0133590 A1 | 5/2019 | Richard |
| 2019/0159782 A1 | 5/2019 | Kamaraj et al. |
| 2019/0223874 A1 | 7/2019 | Pilletere et al. |

FOREIGN PATENT DOCUMENTS

| | | |
|---|---|---|
| CN | 106264647 A | 1/2017 |
| DE | 10116168 A1 | 11/2001 |
| GB | 2353710 A | 3/2001 |
| WO | 2006102578 A1 | 9/2006 |

OTHER PUBLICATIONS

European Search Report dated Dec. 7, 2020, issued in corresponding EP Appln. No. 20189323, 4 pages.

* cited by examiner

STACKABLE LIGATION CLIP

CROSS-REFERENCE TO RELATED APPLICATION

This application claims the benefit of and priority to U.S. Provisional Patent Application No. 62/882,768 filed Aug. 5, 2019, the entire disclosure of which is incorporated by reference herein.

FIELD

This disclosure is directed ligation clips for ligating tissue and, more particularly, to stackable ligation clips for use in multi-fire clip appliers.

BACKGROUND

Ligation clips for ligating tissue are used during a variety of different types of surgical procedures to ligate body vessels. Such ligation clips typically include first and second beams that are pivotably coupled to each other by a hinge portion to facilitate movement of the ligation clips between open and clamped positions. Typically, the ligation clips are supported within a cartridge and removed individually from the cartridge with a single-fire clip applier immediately prior to application of the ligation clip to tissue. This process is time consuming and increases the length of a surgical procedure.

Some ligation clip appliers include clip cartridges that hold a plurality of ligation clips that can be sequentially fed to jaws of the clip applier to allow the clip applier to apply a plurality of clips onto tissue without removing the clip applier from a surgical site or reloading the clip applier with a new ligation clip. These clip appliers are called multi-fire clip appliers. Typically, the ligation clips in multi-fire clip appliers are stacked and aligned in tip-to-tail fashion. The clip applier includes a biasing member positioned at a proximal end of the clip stack to urge the entire stack in a distal direction towards jaws of the clip applier. If the clips in the clip stack become misaligned, the clips become jammed within the clip applier and the clip applier becomes inoperable.

SUMMARY

One aspect of the disclosure is directed to a stackable ligation clip that includes a first beam, a second beam, and a hinge portion. The first beam has a first end, a second end, a first internal clamping surface extending between the first and second ends of the first beam, and an external surface extending between the first and second ends of the first beam. The first beam supports a first alignment member that extends outwardly of the external surface of the first beam and defines a first concavity. The second beam has a first end, a second end, a second internal clamping surface that extends between the first and second ends of the second beam, and an external surface extending between the first and second ends of the second beam. The second beam supports a second alignment member that extends outwardly of the external surface of the second beam and defines a second concavity. The hinge portion couples the first ends of the first and second beams together to facilitate movement of the ligation clip from an open position to a closed position. The first alignment member is configured to receive a portion of the second end of one of the first and second beams of a second ligation clip when the stackable ligation clip is stacked with the second ligation clip in a stacked configuration and the second alignment member is configured to receive a portion of the second end of the other of the first and second beams of the second ligation clip when the stackable ligation clip and the second ligation clip are in the stacked configuration to maintain the stackable ligation clip and the second ligation clip in the stacked configuration.

Another aspect of the disclosure is directed to a plurality of stacked ligation clips including first and second ligation clips. Each of the first and second ligation clips including a first beam, a second beam, and a hinge portion. The first beam has a first end, a second end, a first internal clamping surface extending between the first and second ends of the first beam, and an external surface extending between the first and second ends of the first beam. The first beam also supports a first alignment member that extends outwardly of the external surface of the first beam and defines a first concavity. The second beam has a first end, a second end, a second internal clamping surface extending between the first and second ends of the second beam, and an external surface extending between the first and second ends of the second beam. The second beam supports a second alignment member that extends outwardly of the external surface of the second beam and defines a second concavity. The hinge portion couples the first ends of each of the first and second beams to facilitate movement of each of the first and second ligation clips from an open position to a closed position. In a stacked configuration, the first alignment member of the first ligation clip receives a portion of the second end of one of the first and second beams of the second ligation clip and the second alignment member receives a portion of the second end of the other of the first and second beams of the second ligation clip to maintain the first ligation clip and the second ligation clip in the stacked configuration.

In aspects of the disclosure, the first end of the first beam includes a first locking element and the second end of the second beam includes a second locking element, the first locking element engaging the second locking element when the ligation clip is moved to the clamped position to retain the stackable ligation clip in the clamped position.

In aspects of the disclosure, the first alignment member includes a projection that extends outwardly from the external surface of the first beam and defines the first concavity, wherein the first concavity faces proximally towards the hinge portion.

In some aspects of the disclosure, the second alignment member includes arms that are positioned on sides of the second beam, wherein each of the arms project outwardly from the external side of the second beam and the second concavity is defined in each of the arms and faces proximally towards the hinge portion.

In certain aspects of the disclosure, the second concavity faces proximally towards the hinge portion.

In aspects of the disclosure, the portion of the distal end of the second beam of the second ligation clip received by the first concavity includes a portion of the second locking element.

In some aspects of the disclosure, the first beam supports first bosses and the second beam supports second bosses, wherein the first and second bosses project transversely outwardly of the first and second clamping surfaces.

In certain aspects of the disclosure, the portion of the distal end of the first beam of the second ligation clip received by the first concavity includes a portion of the second locking element.

In aspects of the disclosure, the portion of the distal end of the second beam of the second ligation clip received by the second concavity includes a portion of the first bosses.

Other features of the disclosure will be appreciated from the following description.

BRIEF DESCRIPTION OF THE DRAWINGS

Various aspects of the disclosed stackable ligation clips are described herein below with reference to the drawings, wherein.

DETAILED DESCRIPTION

Figure 1:
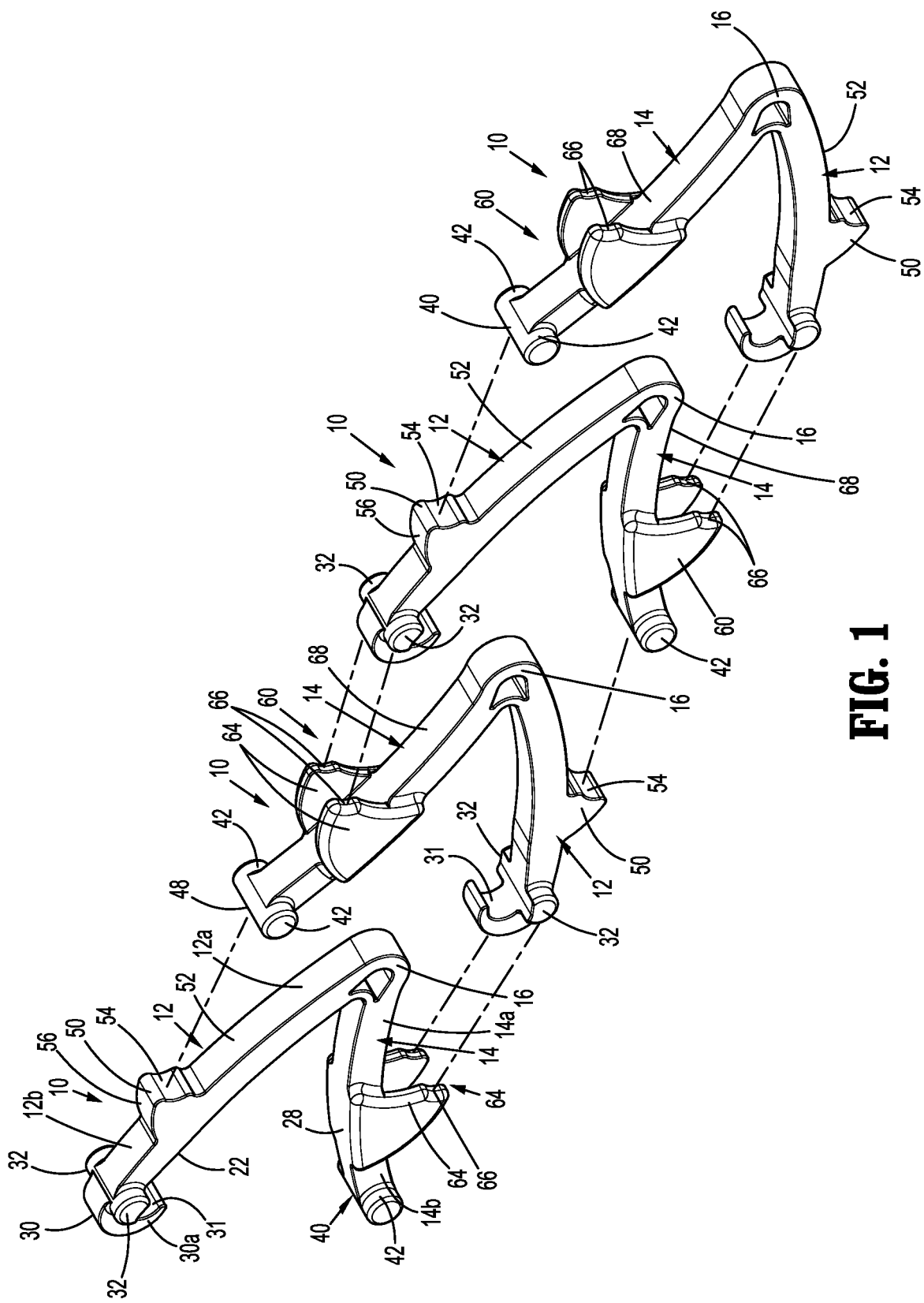
FIG. 1 is a side perspective view of a plurality of stackable ligation clips according to aspects of the disclosure with the ligation clips separated from each other.

The disclosed stackable ligation clips will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The disclosed stackable ligation clips include first and second beams that include an inner clamping surface, an outer surface, a distal end portion, a proximal end portion, and an alignment member. The alignment members are positioned to engage the distal end portions of an adjacent ligation clip when the ligation clips are stacked within a multi-fire clip applier to provide stability to the stack of ligation clips. Providing stability to the clip stack within the multi-fire clip applier allows for a force to be applied to a proximal-most clip in the clip stack to sequentially deliver the clips to jaws of the clip applier. Providing stability to the clip stack within a multi-fire clip applier also minimizes any likelihood that the clips within the clip stack will become misaligned and jam within the clip applier.

The disclosed stackable surgical ligation clips are shown in FIGS. 1-4 generally as ligation clips 10. Each of the ligation clips 10 includes a first beam 12, a second beam 14, and a hinge portion 16. The first and second beams 12, 14 have first ends 12a, 14a, respectively, and second ends 12b, 14b, respectively. The first ends 12a, 14a of the first and second beams 12, 14, are coupled together by the hinge portion 16. In one aspect of the disclosure, the hinge portion 16 forms a living hinge and is integrally formed with the first and second beams 12, 14 to facilitate movement of the ligation clip 10 between an open position and a clamped position as is known in the art. It is envisioned, however, that other hinge configurations may be used to couple the first and second beams 12, 14 of the ligation clip 10 together. In some aspects of the disclosure, the first and second beams 12, 14 of the ligation clip 10 are curved along their longitudinal axes although other beam configurations are envisioned. In certain aspects of the disclosure, the hinge portion 16 defines a through bore 16a that adds flexibility to the ligation clip 10 in the area of the hinge portion 16 and facilitates movement of the first beam 12 in relation to the second beam 14 between the open and clamped positions. In certain aspects of the disclosure, the through bore 16a is crescent-shaped. The through bore 16a also allows for substantially complete closure of the first and second beams 12, 14 in the area adjacent to the second ends 12a, 14a of the beams 12, 14.

The first beam 12 defines a first internal clamping surface 22 that extends between the first and second ends 12a, 12b of the first beam 12 and faces the second beam 14. The second beam 14 defines a second clamping surface 28 that faces the first beam 12. When the ligation clip 10 is in the clamped position, the first clamping surface 22 is in juxtaposed alignment with the second clamping surface 28 to clamp tissue (not shown) between the first and second clamping surfaces 22, 28. Each or both of the first and second clamping surfaces 22, 28, may include retention features (not shown) to minimize tissue slippage between the first and second beams 12, 14 when the ligation clip 10 is in the clamped position. The retention features may include projections or recesses of a variety of configurations in or on the clamping surfaces 22 and/or 28.

The second ends 12b, 14b of the first and second beams 12, 14 form a latching mechanism that includes a first locking element 30 on the first beam 12 and a second locking element 40 on the second beam 14. The first locking element 30 includes a hooked portion 30a that extends downwardly and proximally from the tissue clamping surface 22. The second end 12b of the first beam 12 also includes bosses 32 that protrude transversely outwardly of the first clamping surface 22 of the first beam 12. The bosses 32 are positioned and configured to engage a jaw (not shown) of a clip applier (not shown) to retain the ligation clip 10 within the jaws of the clip applier.

The second locking element 40 defines a cam surface 48 that is configured to deflect the first locking element 30 outwardly over the second locking element 40 to move the first locking element 30 into locking engagement with the second locking element 40 when the ligation clip 10 is moved from the open position to the clamped position. In particular, the cam surface 48 is configured to engage an outer surface 33 (FIG. 2) of the first locking element 30 and deflect the first locking element 30 outwardly in a distal direction past the second locking element 40 as the ligation clip 10 is moved towards the clamped position. After the first locking element 30 passes over the cam surface 48 of the second locking element 40, the first locking element 30 resiliently moves inwardly into engagement with the second locking element 40 to retain the ligation clip 10 in the clamped position. In certain aspects of the disclosure, the cam surface 48 is formed on the second end 14*a* of the second beam 14 and includes a curved, atraumatic surface.

The second end 14*b* of the second beam 14 also includes bosses 42 that protrude transversely outwardly of the second clamping surface 28 of the second beam 14. The bosses 42 are similar to bosses 32 and are positioned and configured to engage a jaw (not shown) of a clip applier (not shown) to retain the ligation clip 10 within the jaws of the clip applier.

The first beam 12 of each of the ligation clips 10 includes a first alignment member 50 that projects outwardly from an external surface 52 of the first beam 12. The first alignment member 50 has a proximally facing surface that defines a concavity 54 (FIG. 1). The concavity 54 receives a distal end of the second beam 14 of a ligation clip 10 that is positioned immediately proximal to the ligation clip 10 when the ligation clips 10 are in a stacked configuration, e.g., in a staple cartridge (not shown) of a multi-clip applier. The distal end of the ligation clips 10 received within the concavity 54 may include the cam surface 48 and/or the bosses 42 of the second beam 14. It is envisioned that the concavity 54 may include a scalloped or rounded surface. Alternately, it is envisioned that the first alignment member 50 may assume a variety of different configurations that can receive a portion of the second beam 14 to maintain alignment between adjacent ligation clips 10 when the ligation clips 10 are in the stacked configuration. The first alignment member 50 may also include a distally facing surface 56 that is smoothly curved to minimize the likelihood of snagging tissue.

Similarly, the second beam 14 of each of the ligation clips 10 includes a second alignment member 60 that projects outwardly of the external surface 62 of the second beam 14. In aspects of the disclosure, the second alignment member 60 may include arms 64 that are positioned on each side of the second beam 14 and project outwardly from the external side of the second beam 14. The arms 64 define proximally facing concavities 66 that are positioned to receive the bosses 32 of first beam 12 when the ligation clips 10 are in the stacked configuration. It is envisioned that the second alignment member 60 may assume a variety of different configurations that can receive the bosses 32 of the first beam 12 to maintain alignment between adjacent stacked ligation clips 10.

Figure 2:
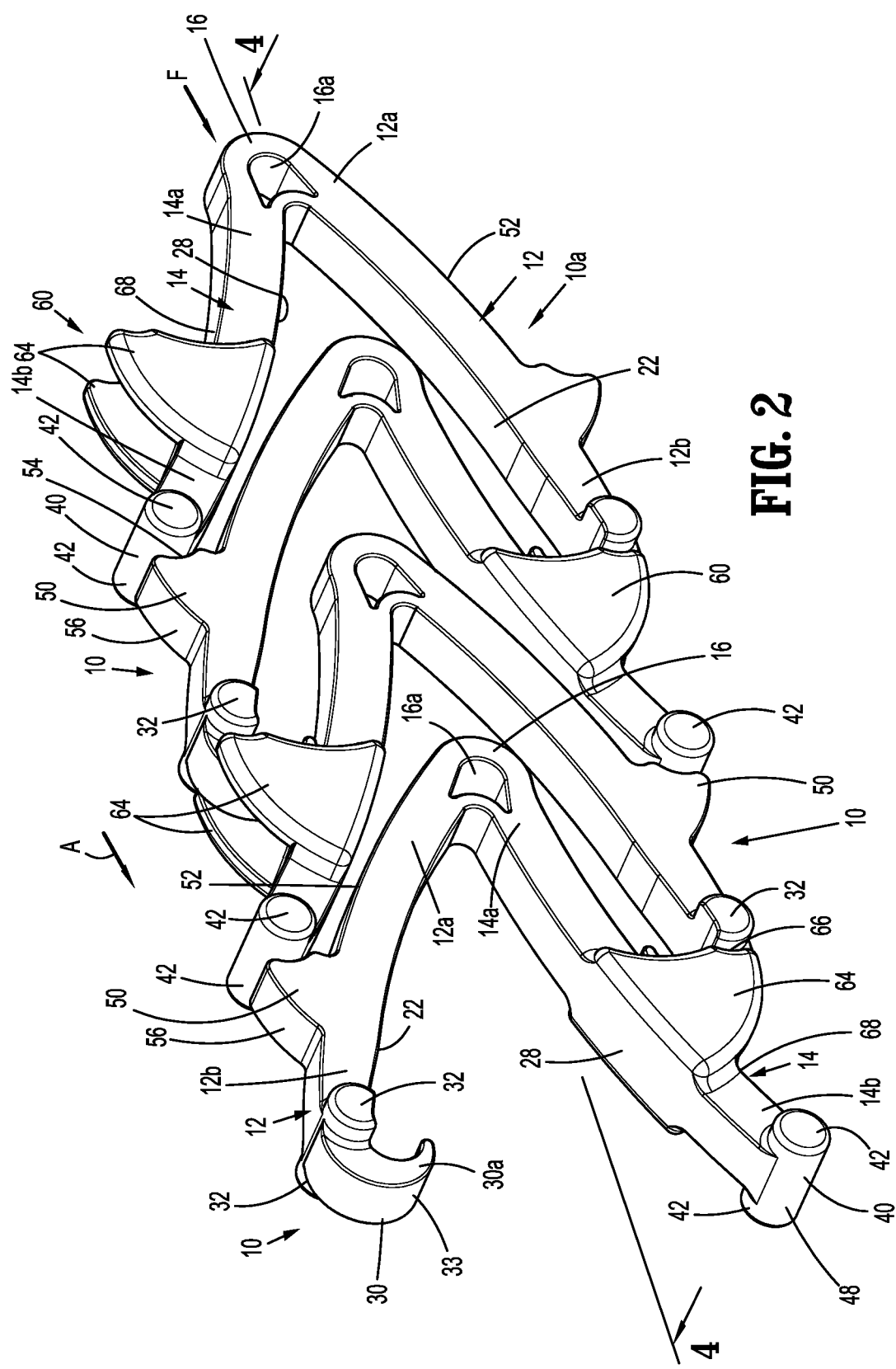
FIG. 2 is a side perspective view from one end of the stackable ligation clips shown in FIG. 1 with the ligation clips in a stacked configuration.
Figure 3:
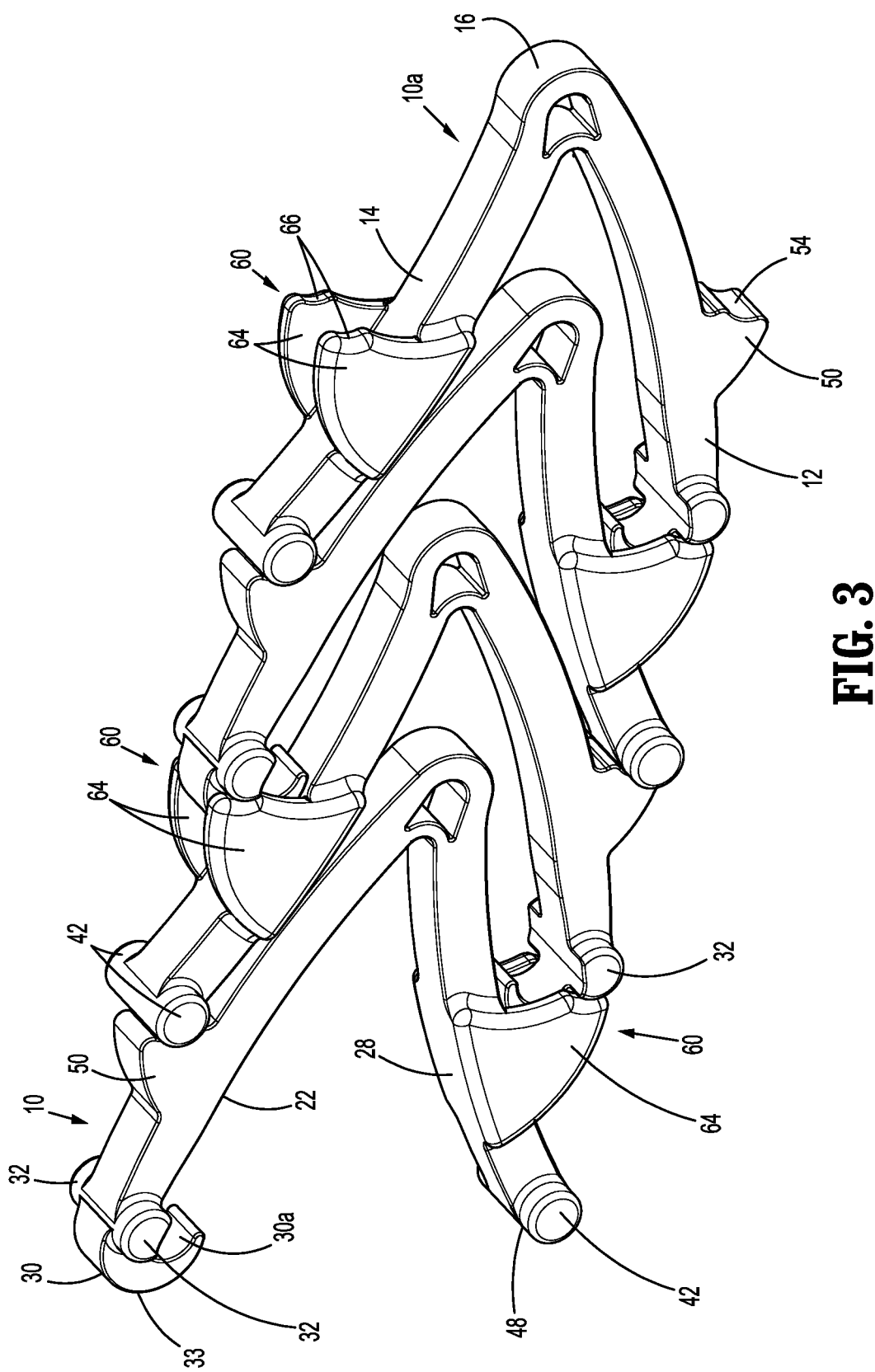
FIG. 3 is a side perspective view from the other end of the stackable ligation clips shown in FIG. 2 with the ligation clips in the stacked configuration.
Figure 4:
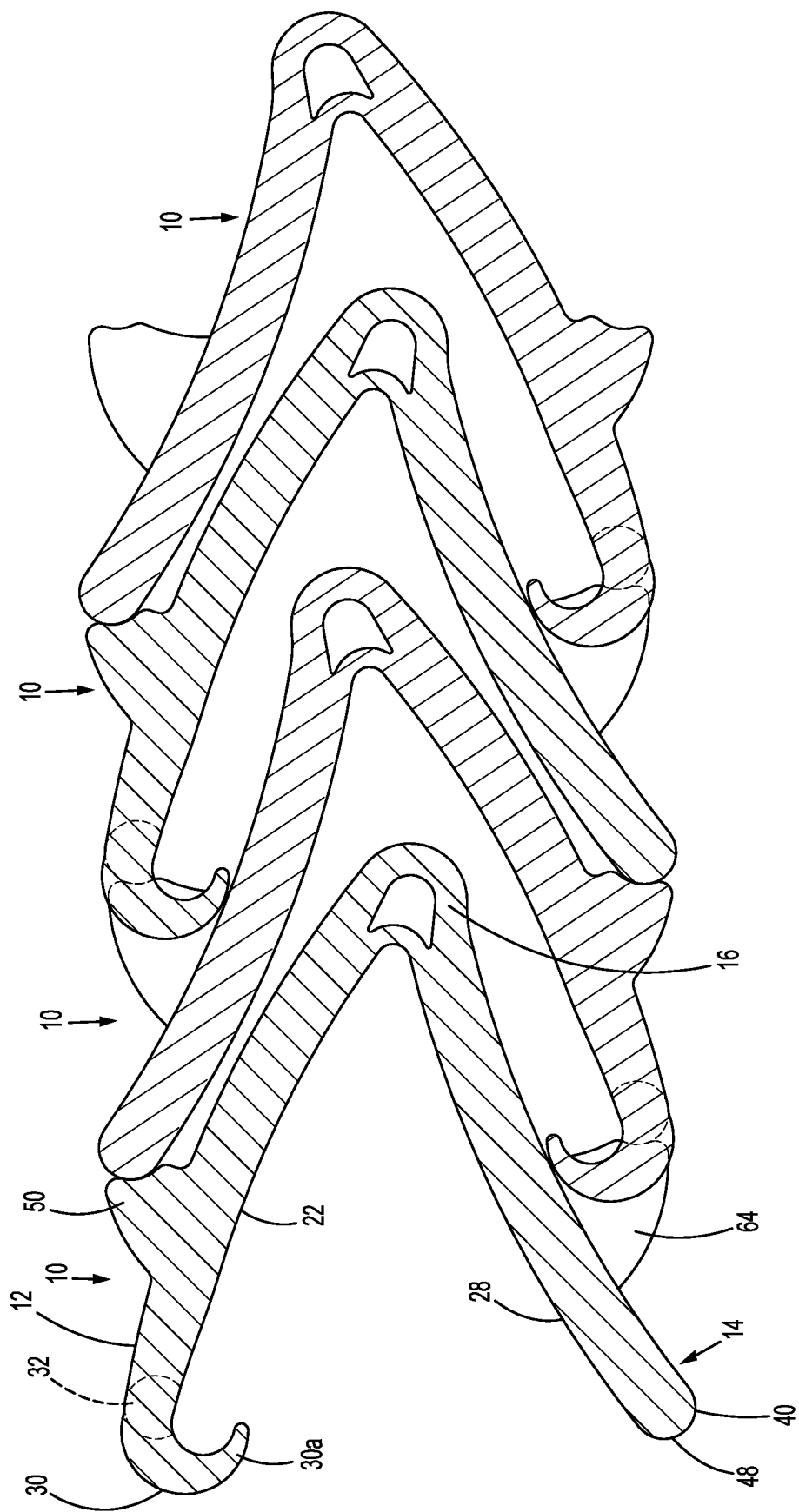
FIG. 4 is a cross-sectional view taken along section line 4-4 of FIG. 2.

FIGS. 2-4 illustrate the ligation clips 10 in a stacked configuration in which the second ends 12*b*, 14*b* of the beams 12 and 14 are positioned distally of the first ends 12*a*, 14*a* of the ligation clips 10 in tip-to-tail fashion. In the stacked configuration, the ligation clips 10 are in the open position with the distal end of the second beam 14 received within the concavity 54 formed in the first alignment member 50 and the bosses 32 on the first beam 12 received within the concavities 66 in the second alignment member 60 of the second beams 14. In the stacked configuration, when a force "F" (FIG. 2) is applied to a proximal-most clip 10*a* of a stack of clips 10 in the direction of arrow "A", the entire stack of clips 10 is moved in unison in the direction of arrow "A". Engagement between the first and second alignment members 50, 60, respectively, and the distal ends of the second and first beams 14, 12, respectively, maintains the clips 10 in longitudinally aligned positions, with the ligation clips in tip-to-tail alignment, to minimize the likelihood that the clip stack will collapse upon application of the force "F" (FIG. 2) to the proximal end of the clip stack.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A stackable ligation clip comprising:
a first beam having a first end, a second end, a first internal clamping surface extending between the first and second ends of the first beam, and an external surface extending between the first and second ends of the first beam, the first beam supporting a first alignment member that extends outwardly of the external surface of the first beam and defines a first concavity;
a second beam having a first end, a second end, a second internal clamping surface extending between the first and second ends of the second beam, and an external surface extending between the first and second ends of the second beam, the second beam supporting a second alignment member that extends outwardly of the external surface of the second beam and defines a second concavity, the second alignment member having arms that project outwardly of the external side of the second beam, the second concavity being defined in each of the arms and facing proximally towards a hinge portion; and
the hinge portion coupling the first ends of the first and second beams together to facilitate movement of the ligation clip from an open position to a closed position;
wherein the first alignment member is configured to receive a portion of a second end of one of a first and second beam of a second ligation clip when the stackable ligation clip is stacked in tip-to-tail fashion with the second ligation clip in a stacked configuration, and the second alignment member is configured to receive a portion of the second end of the other of the first and second beams of the second ligation clip when the stackable ligation clip and the second ligation clip are in the stacked configuration to maintain the stackable ligation clip and the second ligation clip in the stacked configuration.

2. The stackable ligation clip of claim 1, wherein the second end of the first beam of the stackable ligation clip and the second ligation clip includes a first locking element, and the second end of the second beam of the stackable ligation clip and the second ligation clip includes a second locking element, the first locking element engaging the second locking element when the ligation clip is moved to the closed position to retain the stackable ligation clip in the closed position.

3. The stackable ligation clip of claim 2, wherein the portion of the second end of the second beam of the second ligation clip received by the first concavity includes a portion of the second locking element.

4. The stackable ligation clip of claim 2, wherein the first beam of the stackable ligation clip and the second ligation clip supports first bosses, and the second beam of the stackable ligation clip and the second ligation clip supports second bosses, the first and second bosses projecting transversely outwardly of the first and second clamping surfaces.

5. The stackable ligation clip of claim 4, wherein the portion of the second end of the first beam of the second ligation clip received by the first concavity includes a portion of the second locking element.

6. The stackable ligation clip of claim 4, wherein the portion of the second end of the second beam of the second ligation clip received by the second concavity includes a portion of the first bosses.

7. The stackable ligation clip of claim 1, wherein the first alignment member includes a projection that extends outwardly from the external surface of the first beam and defines the first concavity, the first concavity facing proximally towards the hinge portion.

8. A plurality of stacked ligation clips comprising:
a first ligation clip and a second ligation clip, each of the ligation clips including a first beam, a second beam, and a hinge portion, the first beam of each of the ligation clips having a first end, a second end, a first internal clamping surface extending between the first and second ends of the first beam, and an external surface extending between the first and second ends of the first beam, the first beam supporting a first alignment member that extends outwardly of the external surface of the first beam and defines a first concavity;
the second beam of each of the ligation clips having a first end, a second end, a second internal clamping surface extending between the first and second ends of the second beam, and an external surface extending between the first and second ends of the second beam, the second beam supporting a second alignment member that extends outwardly of the external surface of the second beam and defines a second concavity, the second alignment member having arms that project outwardly of the external side of the second beam, the second concavity being defined in each of the arms and facing proximally towards the hinge portion;
the hinge portion of each of the ligation clips coupling the first ends of the first and second beams to facilitate movement of each of the ligation clips from an open position to a closed position;
wherein the first alignment member of the first ligation clip receives a portion of the second end of one of the first and second beams of the second ligation clip when the first ligation clip is stacked with the second ligation clip in a stacked configuration and the second alignment member of the first ligation clip receives a portion of the second end of the other of the first and second beams of the second ligation clip when the first ligation clip and the second ligation clip are in the stacked configuration to maintain the first ligation clip and the second ligation clip in the stacked configuration.

9. The plurality of stacked ligation clips of claim 8, wherein the second end of the first beam of each of the first and second ligation clips includes a first locking element and the second end of the second beam of each of the first and second ligation clips includes a second locking element, the first locking element engaging the second locking element when the first and second ligation clips are moved to their closed positions to retain the first and second ligation clips in their closed position.

10. The plurality of stacked ligation clips of claim 8, wherein the first alignment member of each of the first and second ligation clips includes a projection that extends outwardly from the external surface of the first beam and defines the first concavity, the first concavity facing proximally towards the hinge portion.

11. The plurality of stacked ligation clips of claim 9, wherein the portion of the second end of the second beam of the second ligation clip received by the first concavity includes a portion of the second locking element.

12. The plurality of stacked ligation clips of claim 8, wherein the first beam of each of the first and second ligation clips supports first bosses and the second beam of each of the first and second ligation clips supports second bosses, the first and second bosses projecting transversely outwardly of the first and second clamping surfaces of each of the first and second ligation clips.

13. The plurality of stacked ligation clips of claim 9, wherein the portion of the second end of the first beam of the second ligation clip received by the first concavity includes a portion of the second locking element.

14. The plurality of stacked ligation clips of claim 13, wherein the portion of the second end of the second beam of the second ligation clip received by the second concavity includes a portion of the first bosses.

15. A stackable ligation clip comprising:
a first beam having a first end, a second end, a first internal clamping surface extending between the first and second ends of the first beam, and an external surface extending between the first and second ends of the first beam, the first beam supporting a first alignment member that extends outwardly of the external surface of the first beam;
a second beam having a first end, a second end, a second internal clamping surface extending between the first and second ends of the second beam, and an external surface extending between the first and second ends of the second beam, the second beam supporting a second alignment member that extends outwardly of the external surface of the second beam, the second alignment member having arms that project outwardly of the external side of the second beam; and
a hinge portion coupling the first ends of the first and second beams together to facilitate movement of the ligation clip from an open position to a closed position;
wherein the first alignment member is configured to receive a portion of a second end of one of a first and second beam of a second ligation clip when the stackable ligation clip is stacked in tip-to-tail fashion with the second ligation clip in a stacked configuration, and the second alignment member is configured to receive a portion of the second end of the other of the first and second beams of the second ligation clip when the stackable ligation clip and the second ligation clip are in the stacked configuration to maintain the stackable ligation clip and the second ligation clip in the stacked configuration.

16. The stackable ligation clip of claim 15, wherein the second end of the first beam of the stackable ligation clip and the second ligation clip includes a first locking element, and the second end of the second beam of the stackable ligation clip and the second ligation clip includes a second locking element, the first locking element engaging the second locking element when the ligation clip is moved to the closed position to retain the stackable ligation clip in the closed position.

17. The stackable ligation clip of claim 16, wherein the portion of the second end of the second beam of the second ligation clip received by the first alignment member includes a portion of the second locking element.

18. The stackable ligation clip of claim 16, wherein the first beam supports first bosses, and the second beam supports second bosses, the first and second bosses projecting transversely outwardly of the first and second clamping surfaces.

\* \* \* \* \*